(12) United States Patent
Rigneault et al.

(10) Patent No.: US 8,502,169 B2
(45) Date of Patent: Aug. 6, 2013

(54) DEVICE FOR THE EXALTED DETECTION OF THE EMISSION OF A TARGET PARTICLE

(75) Inventors: Hervé Rigneault, Allauch (FR); Pierre-François Lenne, Marseilles (FR); Jérôme Wenger, Vitrolles (FR); Evgueni Popov, Marseilles (FR); Thomas Ebbesen, Strasbourg (FR)

(73) Assignees: Centre National de la Recherche Scientifique-CNRS, Paris (FR); Universite d'Aix-Marseille, Marseilles (FR)

( * ) Notice: Subject to any disclaimer, the term of this patent is extended or adjusted under 35 U.S.C. 154(b) by 809 days.

(21) Appl. No.: 12/515,664

(22) PCT Filed: Nov. 21, 2007

(86) PCT No.: PCT/FR2007/001913
§ 371 (c)(1),
(2), (4) Date: Jan. 19, 2010

(87) PCT Pub. No.: WO2008/074938
PCT Pub. Date: Jun. 26, 2008

(65) Prior Publication Data
US 2010/0140460 A1 Jun. 10, 2010

(30) Foreign Application Priority Data
Nov. 21, 2006 (FR) ..................................... 06 10178

(51) Int. Cl.
*G01N 21/64* (2006.01)
(52) U.S. Cl.
USPC .............. 250/461.2; 250/363.06; 250/370.02; 250/586; 250/461.1; 435/6.11

(58) Field of Classification Search
USPC ........... 250/370.02, 586, 458.1, 459.1, 461.1, 250/461.2, 363.06
See application file for complete search history.

(56) References Cited

U.S. PATENT DOCUMENTS

| 5,672,514 | A | * | 9/1997 | Tsuchiya et al. ................ 436/86 |
| 2002/0016068 | A1 | * | 2/2002 | Nakano et al. ................ 438/689 |
| 2003/0059798 | A1 | * | 3/2003 | Bryan et al. ...................... 435/6 |
| 2003/0132392 | A1 | * | 7/2003 | Kuroda et al. ................ 250/397 |
| 2004/0008345 | A1 | * | 1/2004 | Nurmikko et al. ............ 356/318 |
| 2005/0214160 | A1 |   | 9/2005 | Weisbuch et al. |
| 2006/0011862 | A1 | * | 1/2006 | Bernstein ................... 250/461.2 |
| 2006/0060766 | A1 |   | 3/2006 | Turner et al. |

* cited by examiner

*Primary Examiner* — Georgia Y Epps
*Assistant Examiner* — Kevin Wyatt
(74) *Attorney, Agent, or Firm* — Arent Fox LLP

(57) ABSTRACT

The invention relates to a device (1) for detecting the emission of a target particle (6) at an emission wavelength, said device comprising: a photo-detector (2, 2A, 2B) comprising a sensitive detection surface having a high optical index; wherein said target particle (6) can be positioned in the vicinity of said sensitive surface in an analysis medium (13) having a low optical index; said device being characterized in that it further comprises: a mask (3) covering said sensitive surface, said mask including at least one area (4) opaque at said emission wavelength and at least one hole (5), said hole being capable of receiving the target particle; and in that the mask includes at least one interface; 7 said device further comprising at least one groove (10, 10A, 10B) provided at said interface, each of said at least one groove surrounding each of said at least one hole.

16 Claims, 9 Drawing Sheets

DEVICE FOR THE EXALTED DETECTION OF THE EMISSION OF A TARGET PARTICLE

CROSS-REFERENCE TO RELATED APPLICATION

This application is a National Stage entry of International Application No. PCT/FR2007/001913, filed Nov. 21, 2007, which claims priority to French Application No. 06/10178, filed Nov. 21, 2006, the disclosure of the prior application is hereby incorporated in its entirety by reference.

The invention relates to a device for the exalted detection of the emission of a target particle at an emission wavelength, said device including:
- a photo-detector comprising a sensitive detection surface having a high optical index;
- said target particle can be positioned in the vicinity of said sensitive surface in an analysis medium having a low optical surface.

Such a device is known from the publication "Opto-electronic DNA Chip: high performance chip reading with an all-electric interface", Frédéric Mallard et al., Biosensors & Bioelectronics, 20 (2005) 1813-1820. This publication teaches a photo-detection matrix of the CMOS type used for receiving probes by grafting, and the probes can receive DNA target molecules by hybridization. Such DNA target molecules can hybridize onto the surface of the matrix using probes positioned on the surface of the matrix. The probes are adapted for receiving the DNA target molecules to be detected. When the DNA target molecules are positioned on the probes by hybridization and once they are rinsed in a manner known per se, the above-mentioned publication teaches to detect the emission of target particles using the photo-detection matrix.

In the above-mentioned device, after the grafting, the probes are aligned at the outer surface of the photo-detector. For an analysis medium including probes having a low optical index, and a photo-detector having a high optical index, the Snells-Descartes laws indicate that it is possible to obtain a detection of the emission of particles in the photo-detector having a high optical index.

The advantage of the above-mentioned device is that it makes it possible to improve the sensitivity of the detection with respect to the known far field detection systems by a camera because of the large solid angle along which the particles see the photo-detector.

However, the sensitivity of the device is not always satisfactory and it is advantageous to further improve the sensitivity of such a device, i.e. increase the quantity of the emission signal of the targeted particles collected in the photo-detector.

One object of the invention is more particularly to improve the device such as described hereabove, with a view to obtaining a better sensitivity.

Therefore, the invention relates to a device such as described hereabove, further including:
- a mask covering such sensitive surface;
- said mask comprising at least one area opaque at said emission wavelength and at least one hole;
- said hole is able to receive said target particle;

wherein said mask includes at least one interface, and said device includes at least one groove positioned at said interface, each of said at least one groove surrounding each of said at least one hole.

According to the invention, for example when a groove is grafted to a device in the vicinity of a sensitive surface in the hole, and when a target particle is hybridized onto the probe, the optical signal emitted by the target particle is confined, which makes it possible to improve the quantity of the collected signal.

More precisely, it has been demonstrated, in the case of the far field detection of fluorescence, that the presence of holes or nano-holes makes it possible to delay the saturation of the fluorescence, while increasing the local excitation intensity in the hole and the radiation yield of the fluorescence, which improves the fluorescence rate per target particle. The publication "Enhancement of Single-Molecule Fluorescence Detection in Sub-wavelength Apertures", Rigneault et al., Physical Review Letters, 11, 117401 2005, illustrates this phenomenon. However, this result is given in the above-mentioned publication only for far field detection.

According to the invention, the exaltation of the emission and of the detection of the target particles is performed for close field detection, i.e. typically for a distance between the hybridized target particle and a grafted probe and a sensitive surface of the photo-detector smaller than the emission wavelength of the target particle.

The advantage of the mask also lies in that the size of the holes can be freely reduced until diameters smaller than the emission wavelength of the target particles are reached. This can make it possible to obtain high densities of emission per surface unit while enabling the detecting of individual particles.

In addition, the detection by the photo-detector is further improved according to the invention thanks to at least one groove positioned at an interface of the mask, each of said at least one groove surrounding each of least one hole.

In addition, according to the invention, the grooves form a circular shape corrugation network and have the double effect of further exalting the light emitted by the target particles and to direct the light emitted by the target particle in one direction or several directions in space. The directivity of the emission and the quantity of the collected signal are thus improved. Thus, the sensitivity of the photo-detector is better.

In addition, when the particle is excited by an excitation beam and the groove is positioned at the interface between the mask and the analysis medium, the device improves the efficiency of the excitation by substantially orienting the excitation beam towards the hole and thus towards the particle to be excited.

The physical effect making it possible to obtain these results is a coupling in plasmon mode at the interface including the groove. Thanks to this plasmon coupling, the light is directed and exalted.

Advantageous embodiments of the invention are given in the appended drawings.

In a known way, for example further to the above-mentioned publication by Mallard, the photo-detector is cut into a plurality of pixels. These pixels form, in a known way, the detection units wherein the electric signal emitted by the photo-electric transformation can be individually detected.

In the photo-detector cut into pixels, a particular problem arises within the scope of the detection of the emission of the target particles.

As a matter of fact, within the photo-detector having a high optical index, the signal emitted by the target particle of a medium having a low optical index and positioned at the interface with the photo-detector having a high optical index, has lobes of emission so that the same particle generates a signal in several pixels of the photo-detector at the same time. The signal detected by a pixel thus does not really correspond to the signal emitted by a target particle. This contrary effect is known as "cross-talk" in English or diaphonie in French.

One embodiment of the invention aims at reducing the cross-talk in a photo-detector such as previously defined and including a plurality of pixels.

Therefor, the photo-detector includes a plurality of pixels and said holes have a dimension which is smaller than the dimension of the pixels of said plurality of pixels, and said mask is so arranged with respect to said photo-detector that each of said at least one hole is positioned opposite a pixel of said plurality of pixels.

Thus, the signal emitted by the target particle grafted to the probe in the hole is confined by the hole and preferably oriented in the pixel. This prevents target particles from emitting into several pixels. The cross-talk between adjacent pixels is thus reduced and the photo-sensitive pixels are efficiently isolated from the free target particles which are not grafted to probes.

The improvement of the directivity of the signal is further particularly advantageous within the scope of a photo-detector according to this embodiment, since it also reduces the cross-talk as previously defined.

In addition, in order to improve the confinement in the hole, said mask is a metallic film in which holes are bored. This makes it possible to obtain the opacity required for the mask for the emission wavelength of the target particle.

In addition, said target particle is able to emit at said emission wavelength, when it is excited by an excitation beam emitted by excitation means and said sensitive surface is such that it is insensitive to such excitation beam.

Particles which must be optically excited for emitting light are called fluorescent particles. In the case of such fluorescent particles, the excitation signal is often an obstacle for the detection of the emission of fluorescence.

Thanks to the above-mentioned embodiment, the emission signal is no longer an obstacle to the detection at the photo-detector, and has no influence on the calculation of the detected emission.

In this case, the groove can be positioned in the path of the excitation beam.

According to one embodiment, the sensitive surface is made insensitive to the emission signal through a rejecting filter positioned between said excitation means and said sensitive surface, said rejecting filter being so arranged as to reject the wavelength of the excitation signal.

Thus, only the emission of particles is detected at the photo-detector, even though an excitation is required for detecting the emission.

In this case, the groove can be advantageously positioned at the interface between the opaque area and the rejecting filter.

Besides, in a known photo-detector, for example in the above-mentioned publication by Mallard, the probes are distributed on the surface of the photo-detector, and the measure of the detected signal is carried out by averaging the signal received on all the probes. This averaging carried out on a large population affects the quality of results.

In order to remedy this drawback, according to one embodiment of the invention, said mask is such that each of said at least one hole can receive only one probe.

Therefore, with very small holes containing only one probe, it is possible to make measurements in an emission mode with individual molecules. Then the above-mentioned averaging effect is reduced.

The invention also relates to a bio-chip including a device such as previously described.

The bio-chip can include at least one probe grafted to said photo-detector, said probe being positioned in said at least one hole.

According to one embodiment, each of said at least one hole includes only one probe.

The bio-chip can also include at least one target particle hybridized to said probe.

The invention also relates to a method for the detection of the emission of the target particle at an emission wavelength including steps consisting in:
providing a device such as previously described;
positioning said particle in said at least one hole;
detecting the emission of said particle using said photo-detector.

The method can also include steps consisting in:
grafting at least one probe in said at least one hole;
hybridizing said target particle onto said probe so as to selectively position said target particle in said hole.

The invention will be better understood when reading the detailed description of at least one embodiment hereinunder and referring to the appended drawings, in which.

In the Figures, identical references represent similar technical elements.

Figure 1:
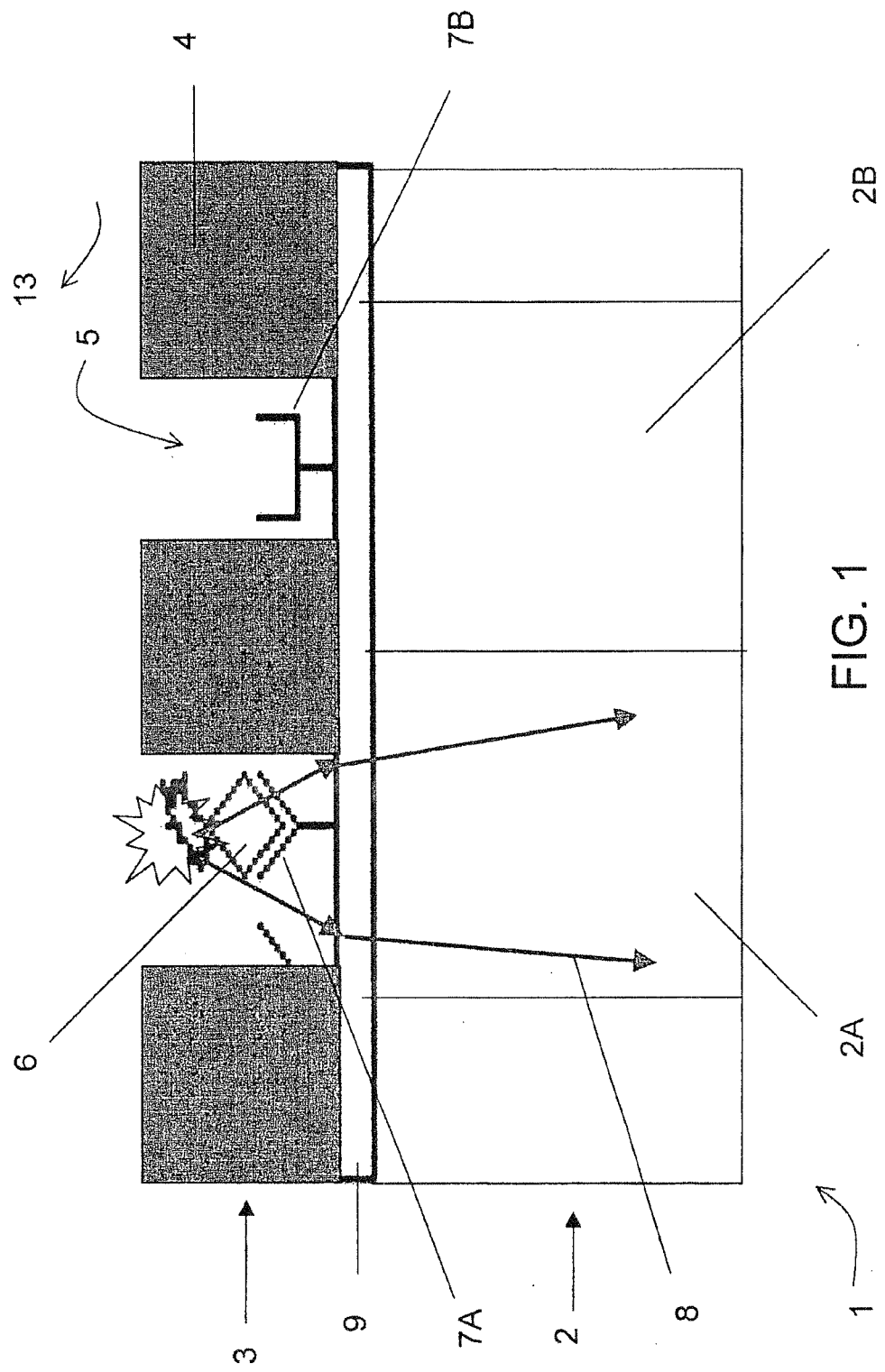
FIG. 1 shows a sectional side view of the device for detecting the emission of the target particle according to the invention.

In FIG. 1 is illustrated a device 1 according to the invention which is suitable for detecting the emission of particle 6.

The particle 6 can be any particle capable of emitting light and more particularly a fluorescent particle, requiring an excitation for emitting light or a chemi-luminescent or bio-luminescent particle not requiring an optical excitation for emitting light. The emission of light can result from thermal emissivity. In the case of a fluorescent particle, the fluorescence can be a parametric fluorescence of the Rayleigh or Hyper-Rayleigh type, or a vibration fluorescence of the spontaneous or stimulated Raman type.

The device 1 includes a photo-detector 2, having an upper surface 9 transparent to the light emitted by the particles 6. The probes 7A, 7B can be fixed to the upper surface 9 by grafting. Within the scope of biological tests, for example for DNA chips, the probes 7A, 7B are molecules grafted onto the upper surface 9. Thanks to an hybridization, target particles 6 are selectively associated with probes 7A, 7B. The emission of the selectively hybridized target particles 6 can then be used for characterizing the target particles 6. In a known way, for example for DNA chips, steps of grafting probes 7A, 7B, hybridizing particles 6, rinsing to keep only the selectively hybridized particles and observing the light emitted by the selectively hybridized particles 6, are carried out.

Within the scope of the invention, the steps of grafting and hybridizing can be carried out by known methods. In addition, a device comprising probes grafted in the vicinity of the sensitive surface of the photo-detector and particles hybridized onto the probes are described, but it should be noted that it is possible to use the device independently of the grafted probes since the detection devices can be with or without any grafted probe.

According to the invention, the device 1 includes a mask 3 covering the photo-detector 2 at the upper surface 9 thereof. The mask 3 includes holes 5 and opaque areas 4. The opaque areas 4 are opaque to the radiation emitted by the target particles 6. In order to reach this opacity, the mask 3 is for example a metallic film made of gold or aluminum, which means that the opaque areas 4 are metallic, made of gold or aluminum. The holes 5 can receive the probes 7A, 7B and leave them within the analysis medium 13. The metallic film in which holes are bored is deposited on the photo-detector 2. The opacity of the metallic film 3 at the emission wavelength of the particles 6 can be obtained by an appropriate selection of the thickness of the film.

The photo-detector 2 is for example a semi-conductor or the CMOS or CCD type. The structure of the photo-detector 2 corresponds for example to a device called APS, which means "Active Pixel Sensor" having a silicon active area. The detection can also be made by optical amplification or amplification of electrons in cascade or avalanche. In FIG. 1, only an active area of the photo-detector 2 is represented. It should be noted that other non-active elements can complete the photo-detector 2.

The silicon active area 2 of the photo-detector 2 has an optical index of approximately 3.5 which is higher than the optical index of the analysis medium 13. The latter has for example an optical index of the order of 1.33 like water at 20° C., or an index of approximately 1 for air. This analysis medium is known in the field of hybridization and detection of target particles emission.

When target particles 6 are fixed on probes 7A, 7B, the effect of this difference in optical index is to allow a satisfactory detection at the photo-detector 2, by emission of a signal in the photo-detector 2. The Snell-Descartes laws or the theory of electromagnetism make it possible to confirm this assertion.

During the emission of target particles 6, the opaque area 4 makes it possible to confine the signal 8 emitted to the photo-detector 2, so the detection is improved.

The photo-detector 2 can be cut into pixels 2A, 2B corresponding to distinct detection units. The photo-detector APS such as mentioned hereabove includes for example a 640× 480 pixels matrix with a dimension of 5.6 micrometers by 5.6 micrometers.

The holes 5 of the mask 3 are advantageously positioned above each of the pixels and their dimension is smaller than the dimensions of the pixels.

In the case of the dimensions of the above-mentioned pixels, the holes have for example dimensions of the order of a few hundreds of nanometers by a few hundreds of nanometers. The mask 3 is in this case a metallic film in which nano-holes 5 are bored.

The opaque areas 4 of the film 3 then confine the emission of the target particles 6 to each of the pixels. The signal 8 emitted by a particle to a pixel is slightly deviated to the adjacent pixels, so that the cross-talk between the pixels is reduced.

Figure 2:
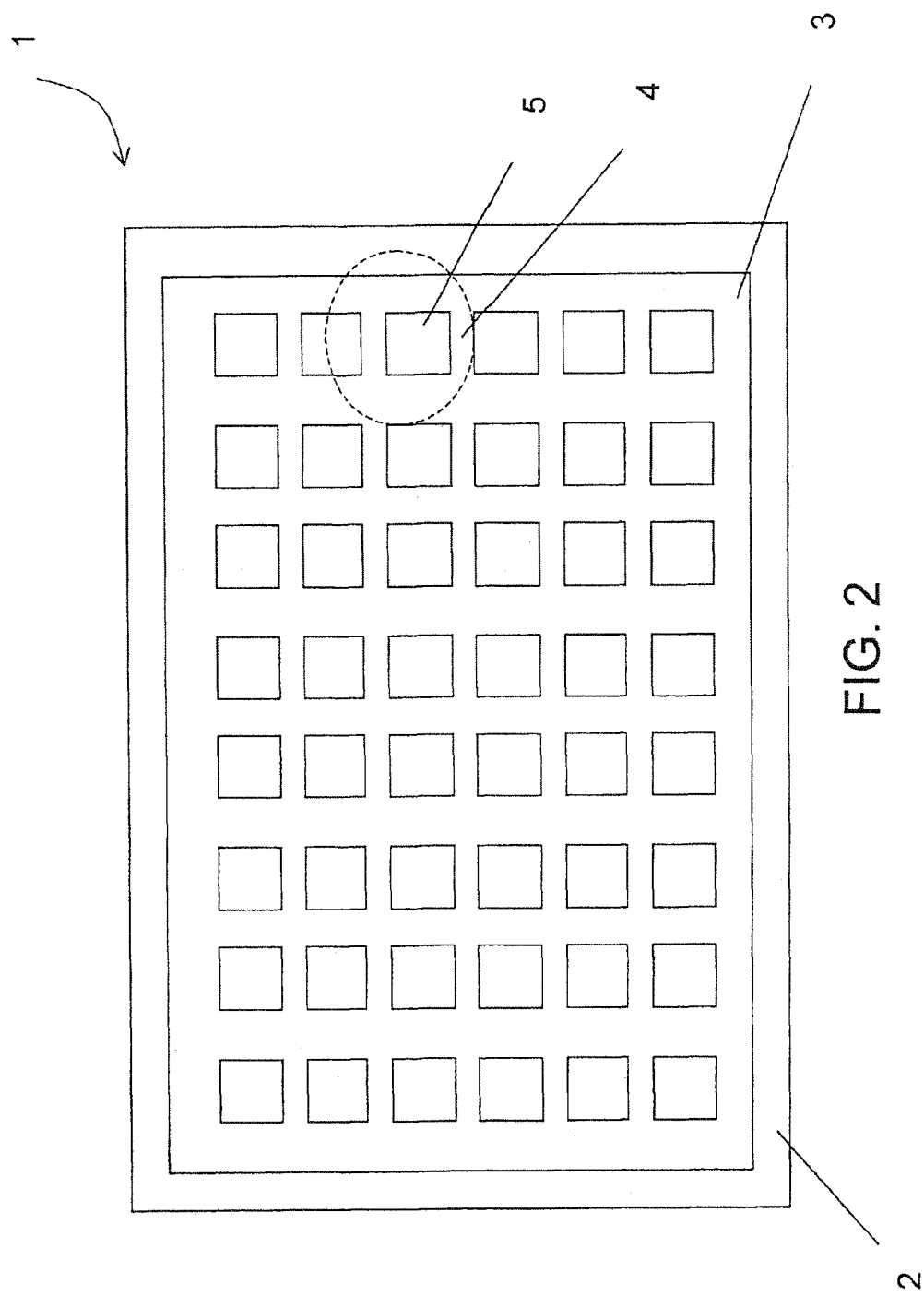
FIG. 2 shows a top view of the device of FIG. 1.

A top view of the device 1 is illustrated in FIG. 2. The metallic mask 3 covering the photo-detector 2 can be seen. The mask 3 includes holes 5 and opaque areas 4. The structure of the opaque areas 4 will be described in greater details in the following for a particular embodiment of the invention.

Figure 3:
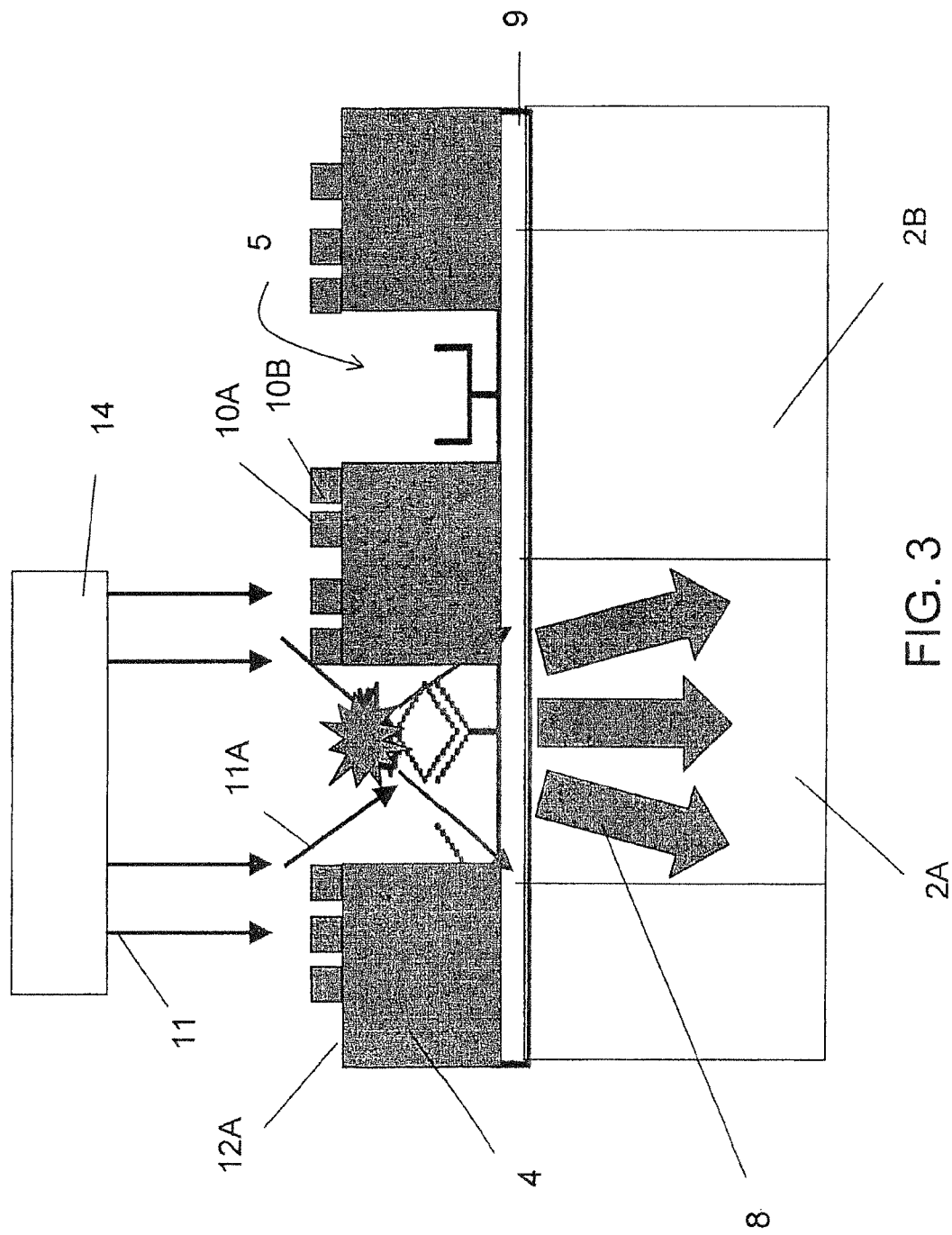
FIG. 3 shows a sectional side view of a particular embodiment of the device of FIG. 1.

FIG. 3 is a side view of the device 1 according to a particular embodiment of the invention, in a first configuration.

In FIG. 3, the particle 6 hybridized to a probe 7A is a fluorescent particle, excited by an excitation laser 14 emitting an excitation beam 11, but it should be noted that the embodiment which will be described can be identical in the case of a bio-luminescent or chemi-luminescent. In the case of an excitation by an excitation beam 11, the metallic film 3 is preferably also opaque at the wavelength of the excitation beam.

In FIG. 3, the opaque areas 4 include a groove formed of low areas 10B and high areas 10A. The groove 10 preferably forms a circular corrugation about the hole 5. The high areas 10A can be slot shaped like in FIG. 3, but they can also have another shape, for example a sinusoidal or a triangular shape. The high and low areas 10A and 10B can be arranged according to a linear or non-linear progressing spacing.

The groove 10 is positioned on the upper surface of the opaque area 4 contrary to the side surface of the opaque area forming the hole 5.

According to this embodiment, the excitation beam 11 is intercepted by the groove 10. The groove 10 is positioned at the interface between the analysis medium 13 and the opaque area 4. The groove 10 generates a plasmon type coupling mode between the analysis medium 13 in contact with the groove, the opaque area 4 which confines the excitation beam 11 to the particle 6. This confinement phenomenon is illustrated by oblique arrows 11A in FIG. 3. The efficiency of the excitation is thus improved in this embodiment. This embodiment is thus particularly advantageous in the case of a fluorescent particle in order to improve the quality of the excitation.

In addition, as mentioned hereabove, the opaque area 4 also confines a light emitted to the photo-detector 2. The assembly thus improves the efficiency of the excitation and the emission and thus the global quality of the detection according to the invention.

Figure 4:
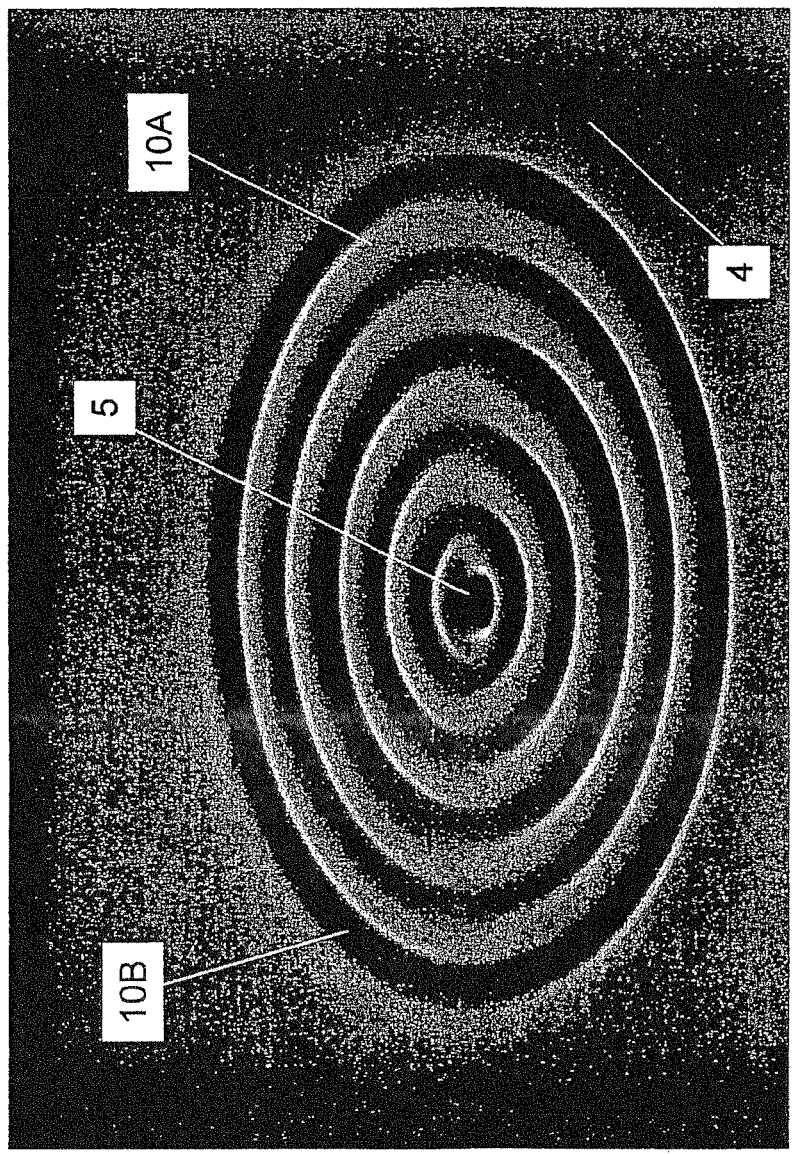
FIG. 4 shows a top photographic view of the grooves used in the embodiment of FIG. 3.

FIG. 4 shows a photographic view of the groove 10, on which the hole 5 surrounded by a succession of high areas 10A and low areas 10B can be seen. The groove is formed at the surface of the opaque area 4.

Figure 5:
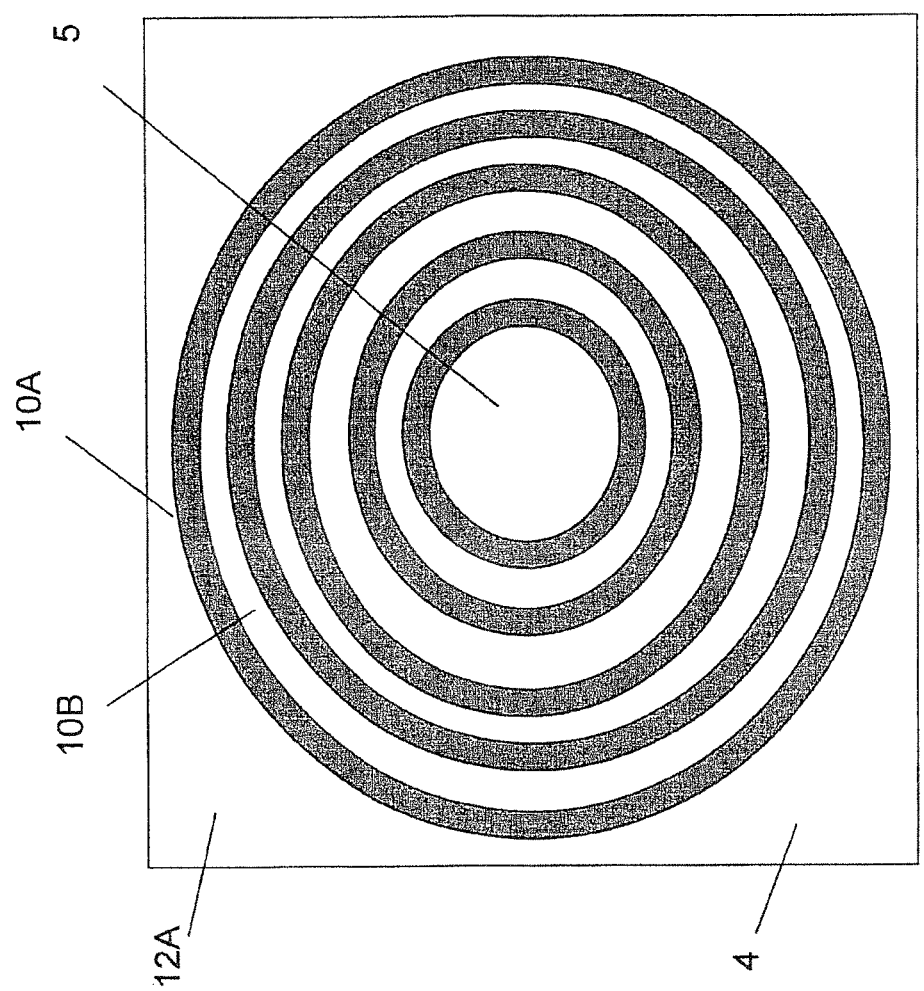
FIG. 5 shows a schematic view of the photographic view of the FIG. 4.

FIG. 5 is a schematic representation of the groove 10 on which the hole 5 surrounded by a succession of high areas 10A and low areas 10B can be seen. The groove is formed at the upper surface 12A of the opaque area 4.

An example of the dimensions of the mask 3 including the groove 10 is provided, it being understood that these dimensions are not limitative within the scope of the invention. The wavelength emitted by the particle 6 is of the order of 500 nanometers. The hole 5 is for example circular with a diameter of 250 to 200 nanometers. The height of the mask 3 is greater than the height of the probe 7A, 7B, so that the opaque area 4 hides the light emitted by the particle 6 when it is fixed to the probe 7A, 7B. The opaque area 4 or in an equivalent way the hole 5 thus has a height of approximately 200 nanometers. The groove 10 which means the high areas 10A or in an equivalent way the low areas 10B has a height of approximately 50 nanometers. The pitch separating the high areas and the low areas approximately amounts to 80 nanometers.

Figure 6:
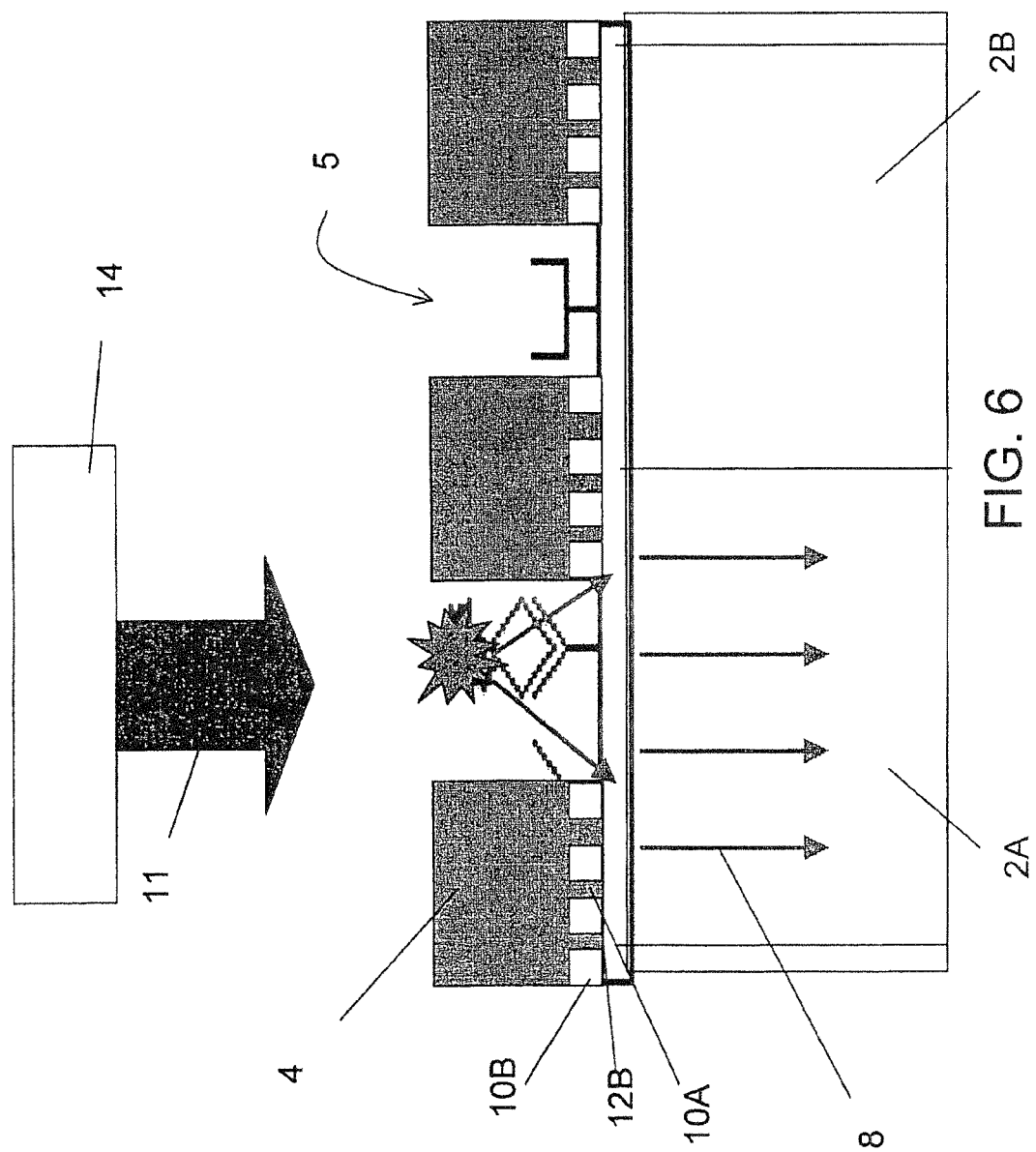
FIGS. 6 to 8 show sectional side views of particular embodiments of the device of FIG. 1.

FIG. 6 illustrates another configuration of the device 1 according to the invention, wherein the groove 10 is positioned at the interface between the opaque area 4 and the upper surface of the photo-detector 2, at the lower surface 12B of the opaque area 4. The groove 10 includes, as previously mentioned, high areas 10A and low areas 10B. This time, the directivity of the light emitted by the particle 6 is improved. This is true whether the particle 6 is excited or not. According to this embodiment, the plasmon coupling effect by the groove 10 between the opaque area 4 and the analysis medium 13 at the hole 5, enables an improved confinement of the light and an increased directivity to the photo-detector 2 and more particularly to the pixel 2A of the photo-detector positioned under the hole 5.

Figure 7:
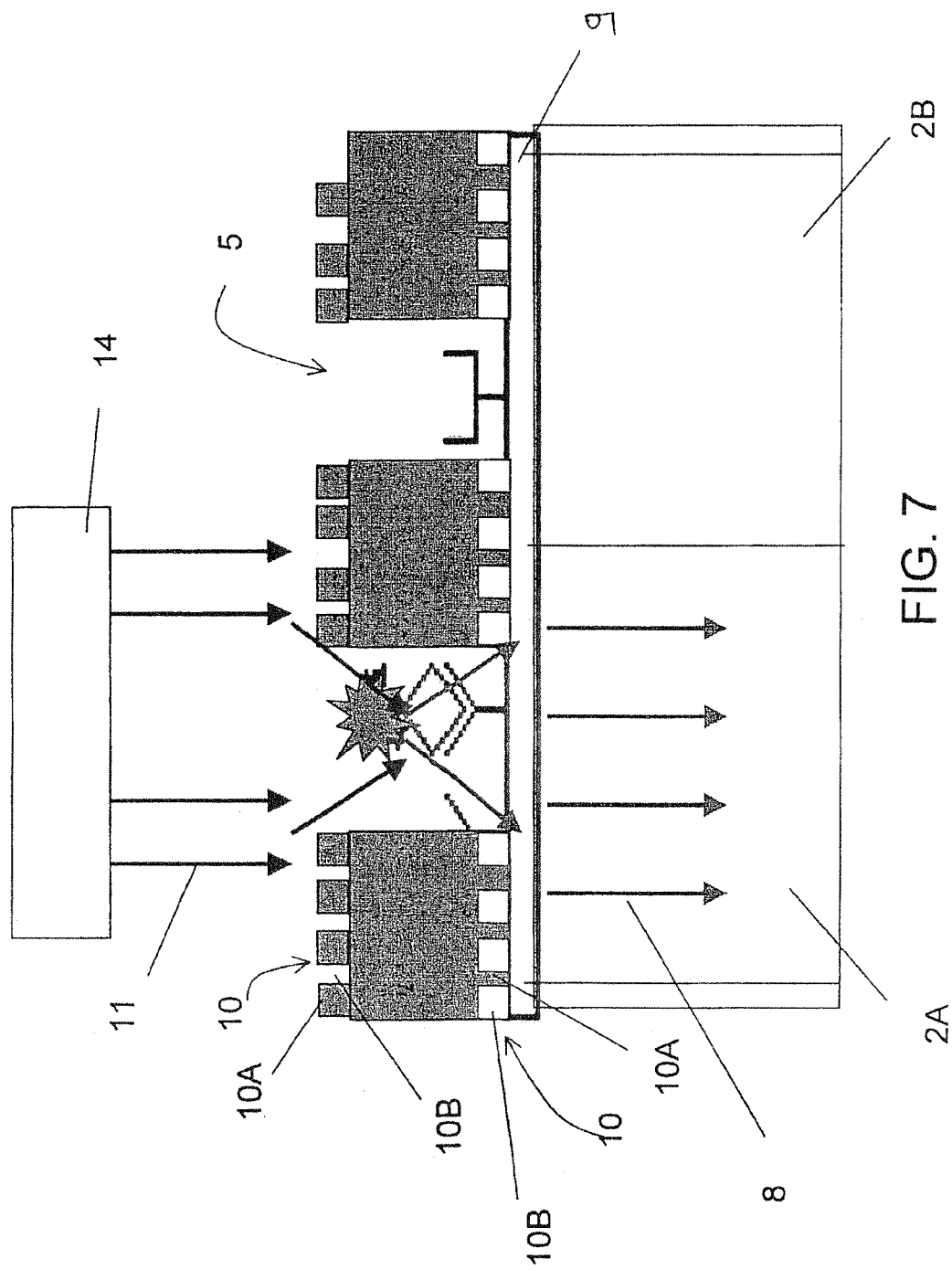

Two previously described embodiments are illustrated in FIG. 7, which can be combined so as to improve the directivity of the light emitted by the particle 6 and the directivity of the excitation by the excitation beam 11. In this case, a first groove 10 is positioned at the interface between the opaque area 4 and the analysis medium 13, and a second groove 10 is positioned at the interface between the opaque area 4 and the upper surface 9 of the photo-detector 2. The upper surface 12A and the lower surface 12B of the opaque area 4 thus include each a groove forming a circular corrugation around the hole 5.

Figure 8:
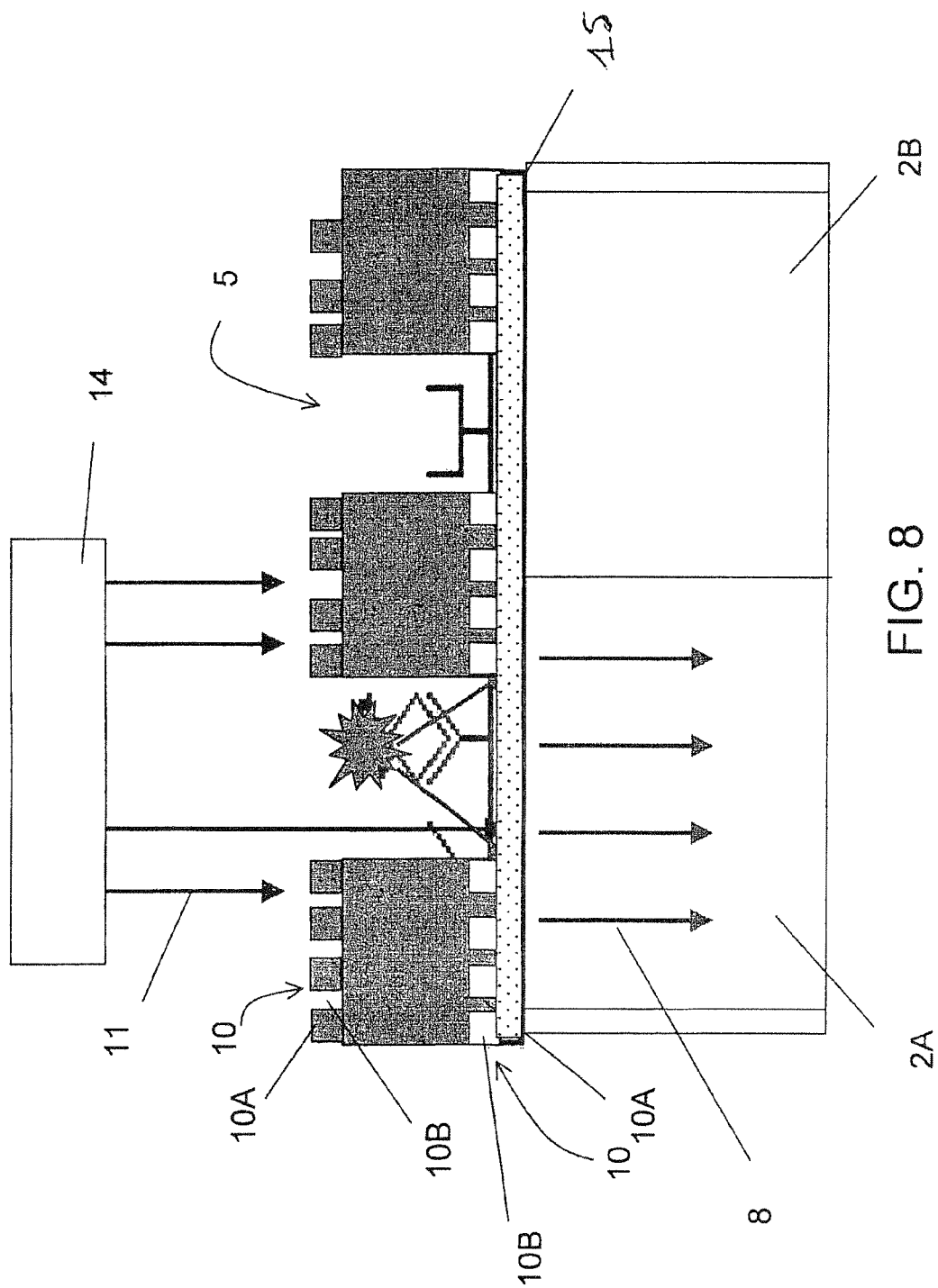

FIG. 8 illustrates a particular embodiment of the invention wherein the device includes a rejecting filter 15. This rejecting filter 15 is capable of filtering the wavelength or the range of wavelength of the excitation beam 11, so as not to affect the detection of the light emitted by the particle 6 when it is at a different wavelength. The rejecting filter 15 can form the upper surface of the photo-detector 2 like in FIG. 8 or be positioned in contact with this upper surface 9 or even be included in the photo-detector 2.

In an alternative solution, so as not to affect the detection of the light emitted by the particle 6, the photo-detector 2 itself is selected so as to be insensitive at the wavelength or at the range of the wavelength of the excitation beam 11.

Figure 9:
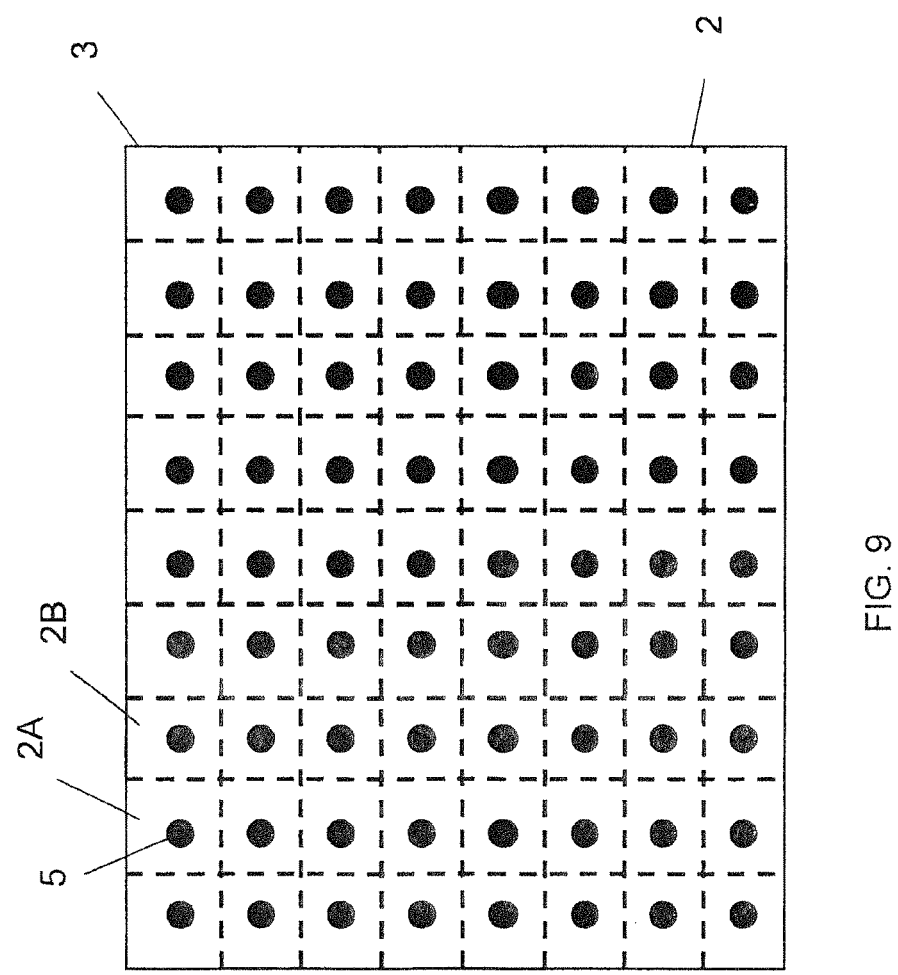
FIG. 9 is a top view of a particular embodiment of the device of FIG. 1.

FIG. 9 illustrates a bottom view of an embodiment of the device 1 according to the invention, wherein the matrix of pixels 2A, 2B is illustrated in dotted lines for the photo-detector 2 whereon the mask has been positioned. In an advantageous way, the mask 3 is such that only one hole 5 is positioned opposite each pixel 2A, 2B. Thus, the cross-talk between the adjacent pixels is reduced.

In addition, the dimension of the hole 5 can be such that only one probe is positioned in the hole 5 during the grafting. Thus, the light detected by a pixel substantially corresponds to the light emitted by only one particle which makes it possible to omit the averaging effects.

All the above-mentioned embodiments can then be applied to such a configuration wherein the photo-detector 2 includes a plurality of pixels corresponding to a plurality of photo-detectors in parallel. In particular, the embodiments wherein the mask 3 includes grooves 10 can advantageously be used for a matrix of pixels so as to reduce the cross-talk between the pixels.

Such a matrix of pixels can be continuously operated when the optical signal emitted by the target particles 6 is detected when integrating the signal for each pixel or group of pixels of the photo-detector 2. Photometric measurements can also be carried out.

The matrix of pixels can also be operated in a pulse mode wherein the signal is integrated on short time ranges with respect to the time characteristic of the phenomenon to be studied. The analysis of the resulting track thus gives information on the molecular association to be studied. This operation mode is for example used in the case of a fluorescence correlation spectroscopy, the imaging of the fluorescence lifetime or the transfer of energy by fluorescence resonance.

The device 1 such as previously described can advantageously be used as a detector in a bio-chip, for example a DNA or a protein bio-chip. In this case, the bio-chip includes probes 7A, 7B grafted in holes 5 for receiving the target particles 6.

It can also be used as a bacterial presence detector, for example for food tests.

The invention claimed is:

1. A device for detecting an emission of a target particle at an emission wavelength, said device comprising:

a photo-detector comprising a sensitive detection surface having a high optical index, said target particle being a fluorescent particle and positioned in the vicinity of said sensitive surface in an analysis medium having a low optical index;

a mask covering said sensitive surface, said mask including: at least one area opaque at said emission wavelength, at least one hole being capable of receiving said target particle, and at least one interface; and at least one groove provided at said interface, each of said at least one groove forming a circular corrugation surrounding each of said at least one hole, wherein the device is configured to perform close field detection of the emission of the target fluorescent particle.

2. A device according to claim 1, wherein said groove is positioned at the interface between said opaque area and said analysis medium.

3. A device according to claim 1, wherein said groove is positioned at the interface between said opaque area and a surface of said photo-detector.

4. A device according to claim 1, wherein said photo-detector includes a plurality of pixels and wherein said at least one hole has a dimension smaller than that of the pixels of said plurality of pixels, and said mask is arranged with respect to said photo-detector, so that each one of said at least one hole is positioned opposite a pixel of said plurality of pixels.

5. A device according to claim 1, wherein said opaque mask is a metallic film.

6. A device according to claim 1, wherein said target particle is able to emit at said emission wavelength upon being excited by an excitation beam emitted by excitation means and said sensitive surface is configured to be insensitive to said excitation beam.

7. A device according to claim 6, wherein said at least one groove is positioned in the path of said excitation beam.

8. A device according to claim 6, wherein said device includes a rejecting filter positioned between such excitation means and said sensitive surface, the rejecting filter being arranged to reject the wavelength of the excitation beam.

9. A device according to claim 8, wherein said groove is positioned at the interface between said opaque area and said rejecting filter.

10. A device according to claim 1, wherein said photo-detector is a silicon semi-conductor.

11. A bio-chip including a device according to claim 1.

12. A bio-chip according to claim 11 including at least one probe grafted to said photo-detector, said probe being positioned in said at least one hole.

13. A bio-chip according to claim 12, wherein each of said at least one hole includes a single probe.

14. A bio-chip according to one of claim 12 or 13 comprising at least one target particle hybridized to said probe.

15. A method for detecting an emission of a target particle at an emission wavelength, comprising:

providing a device comprising:

a photo-detector comprising a sensitive detection surface having a high optical index, said target particle being a fluorescent particle and positioned in the vicinity of said sensitive surface in an analysis medium having a low optical index;

a mask covering said sensitive surface, said mask including: at least one area opaque at said emission wavelength, at least one hole being capable of receiving said target particle, and at least one interface; and at least one groove provided at said interface, each of said at least one groove forming a circular corrugation surrounding each of said at least one hole;

positioning said particle into said at least one hole; and
performing a close field detection of the emission of said particle using said photo-detector.

16. A method for detecting the emission of a target particle according to claim 15, further comprising:
grafting at least one probe in said at least one hole; and
hybridizing said target particle onto said probe so as to position said target particle in said hole.

* * * * *